United States Patent [19]

Hall et al.

[11] Patent Number: 4,661,506
[45] Date of Patent: Apr. 28, 1987

[54] 7-OXABICYCLOHEPTANE SUBSTITUTED OX PROSTAGLANDIN ANALOGS

[75] Inventors: Steven E. Hall, Ewing Township, Mercer County; Martin F. Haslanger, Lambertville; Ravi K. Varma, Belle Mead, all of N.J.

[73] Assignee: E. R. Squibb & Sons, Inc., Princeton, N.J.

[21] Appl. No.: 677,131

[22] Filed: Nov. 30, 1984

[51] Int. Cl.$^4$ .................... C07D 493/08; A61K 31/34
[52] U.S. Cl. .................... 511/382; 548/252; 549/463; 514/469
[58] Field of Search .............. 549/463; 548/252; 514/382, 469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,351,949 | 9/1982 | Larock | 548/359 |
| 4,458,091 | 7/1984 | Jones | 502/502 |
| 4,582,854 | 4/1986 | Hull | 514/469 |

FOREIGN PATENT DOCUMENTS

| | | | |
|---|---|---|---|
| 0043292 | 8/1982 | European Pat. Off. | 549/463 |
| 2039909 | 8/1980 | United Kingdom | 549/463 |

Primary Examiner—Robert Gerstl

Attorney, Agent, or Firm—Lawrence S. Levinson; Burton Rodney

[57] ABSTRACT

7-Oxabicycloheptane substituted oxo prostaglandin analogs are provided having the structural formula

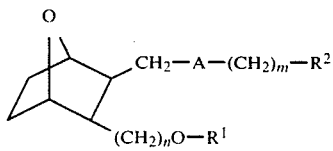

wherein $R^1$ is lower alkyl, aryl, aralkyl, cycloalkyl or cycloalkylalkyl, A is —CH=CH— or —(CH$_2$)$_2$—, n is 1 to 4, m is 1 to 8, and $R^2$ is

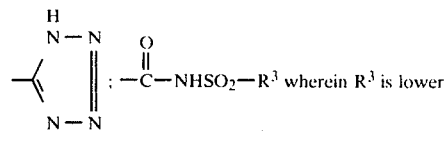 ; —C—NHSO$_2$—R$^3$ wherein R$^3$ is lower alkyl, aryl or arylalkyl; or 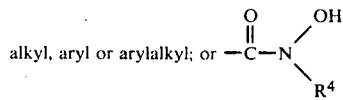

wherein $R^4$ is H or lower alkyl and including all stereoisomers thereof.

The compounds are cardiovascular agents useful, for example, in the treatment of thrombotic disease.

19 Claims, No Drawings

7-OXABICYCLOHEPTANE SUBSTITUTED OX PROSTAGLANDIN ANALOGS

DESCRIPTION OF THE INVENTION

The present invention relates to 7-oxabicycloheptane oxa prostaglandin analogs which are cardiovascular agents useful, for example, in the treatment of thrombotic disease. These compounds have the structural formula

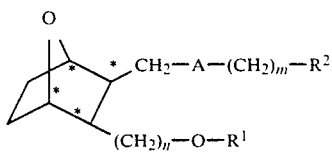

and including all stereoisomers thereof, wherein A is $CH=CH$ or $(CH_2)_2$; m is 1 to 8, n is 1 to 4; $R^1$ is lower alkyl, aryl, aralkyl, lower alkenyl, cycloalkyl or cycloalkylalkyl; and $R^2$ is

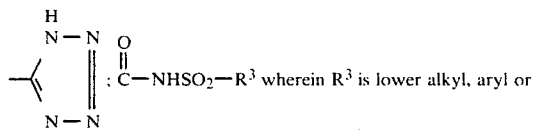

arylalkyl; or $-\overset{O}{\overset{\|}{C}}-\overset{OH}{\overset{|}{N}}-R^4$ wherein $R^4$ is H or lower alkyl;

but where $R^2$ is 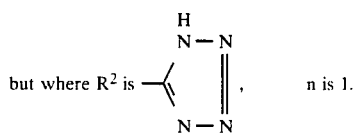, n is 1.

The term "lower alkyl" or "alkyl" by itself or as part of another group as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an alkylthio substituent, an alkylamino substituent (e.g., $R^3NH-$ or $(R^3)_2N-$ wherein $R^3$ is lower alkyl), a haloaryl substituent, a cycloalkyl substituent (that is, cycloalkylalkyl) or an alkylcycloalkyl substituent.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" by itself or as part of another group as emloyed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" by itself or as part of another group as used herein refers to lower alkyl groups as discussed above having an aryl substituent, such as benzyl.

The terms "$(CH_2)_m$" and "$(CH_2)_n$" include a straight or branched chain radical having from 1 to 8 carbons in the normal chain in the case of "$(CH_2)_m$" and 1 to 4 carbons in the normal chain in the case of "$(CH_2)_n$" and may contain one or more lower alkyl substituents. Examples of $(CH_2)_m$ groups and $(CH_2)_n$ groups (where appropriate) include $CH_2$,

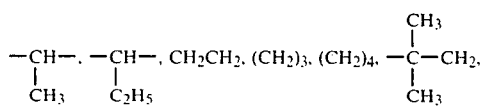

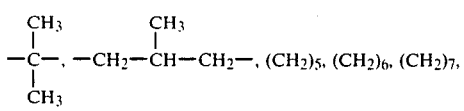

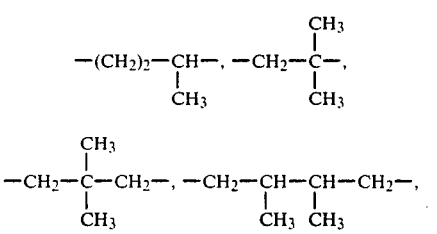

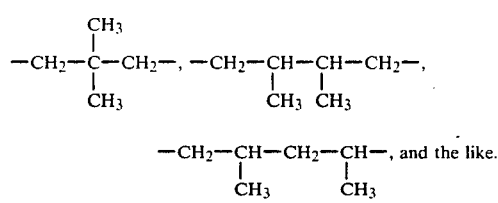

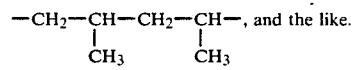, and the like.

Preferred are those compounds of formula I wherein A is $(CH_2)_2$ or $CH=CH$, $(CH_2)_m$ is

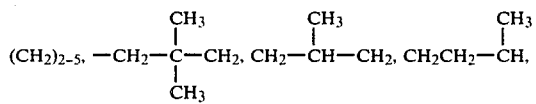

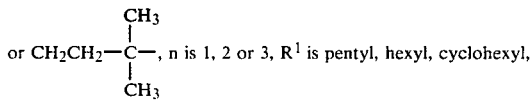, n is 1, 2 or 3, $R^1$ is pentyl, hexyl, cyclohexyl, cyclohexylmethyl, phenyl, benzyl, 2-phenylethyl or 3-phenylpropyl, and $R^2$ is 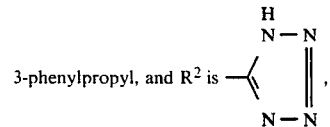,

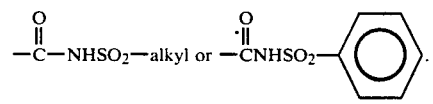

The various compounds of the invention may be prepared as outlined below.
A. Where n = 1, A is —CH=CH— and R² is 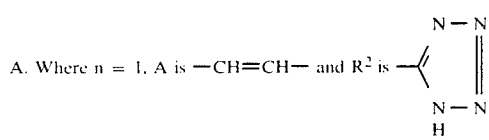
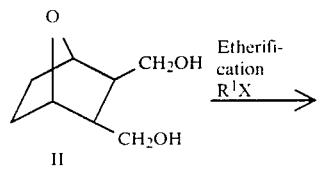
II
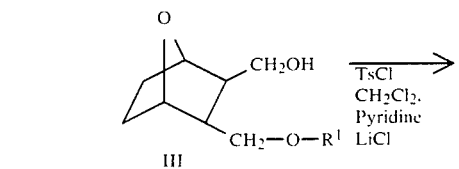
III
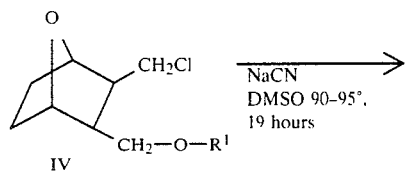
IV
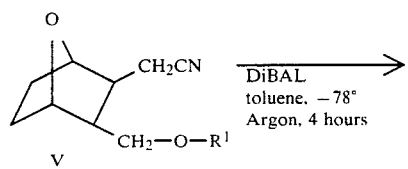
V
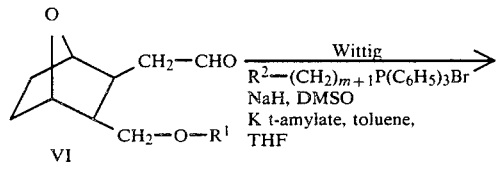
VI
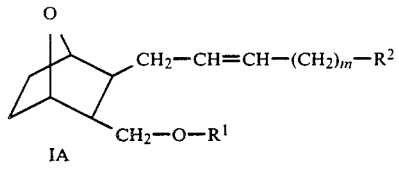
IA
B. Where n = 1, A is —(CH₂)₂— and R² is 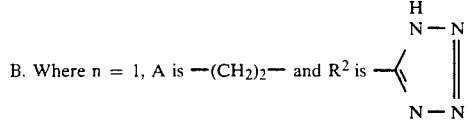
IA $\xrightarrow{\text{Reduction}}_{\text{H}_2/\text{Pd/C}}$ 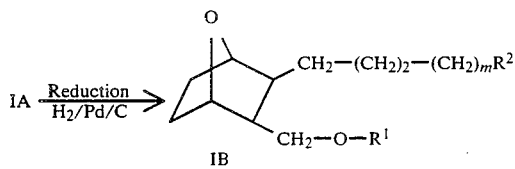
IB
C. Where n = 1, A is —CH=CH—, R² is —C(=O)—NHSO₂—R³ 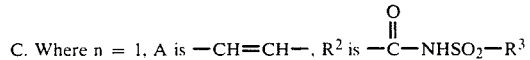
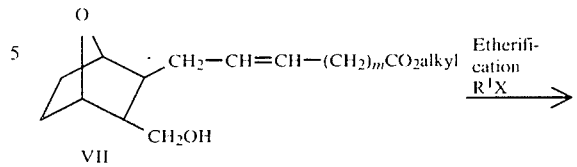
VII
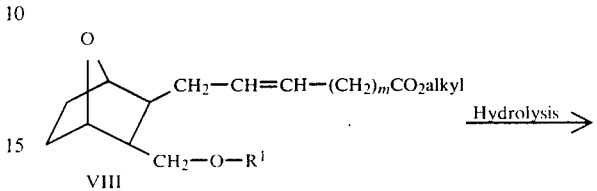
VIII
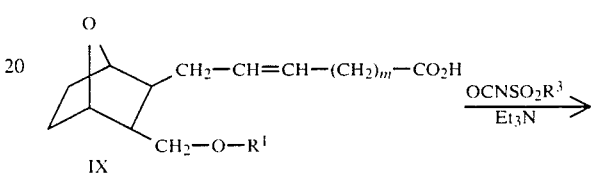
IX
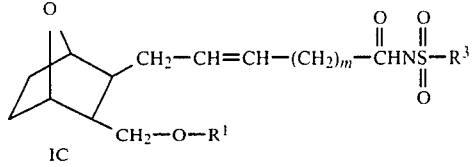
IC
D. Where n = 1, A is —(CH₂)₂—, R² is —C(=O)NHSO₂—R³
VII $\xrightarrow{\text{Reduction}}_{\text{H}_2/\text{Pd/C}}$
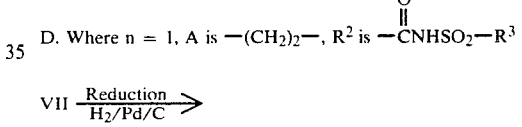
VIIA
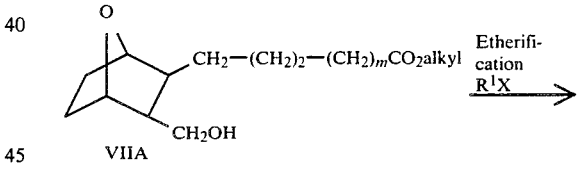
VIIIA
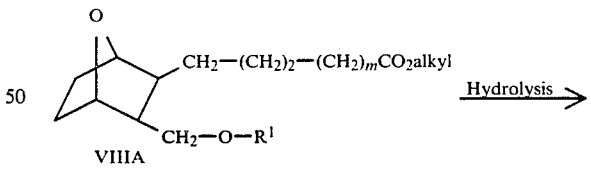
IXA
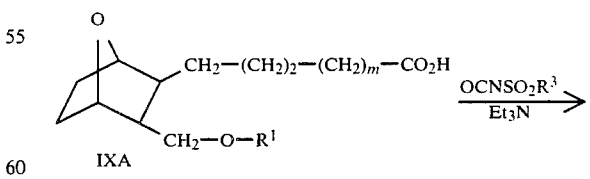
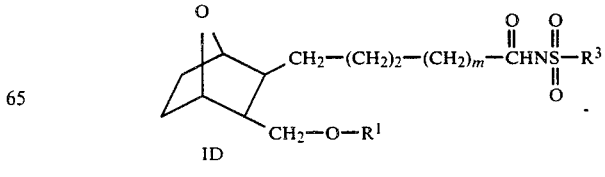
ID E. Where n is 1, A is CH=CH or (CH₂)₂, R² is $-\text{C}(=O)-\text{N}(OH)(R^4)$

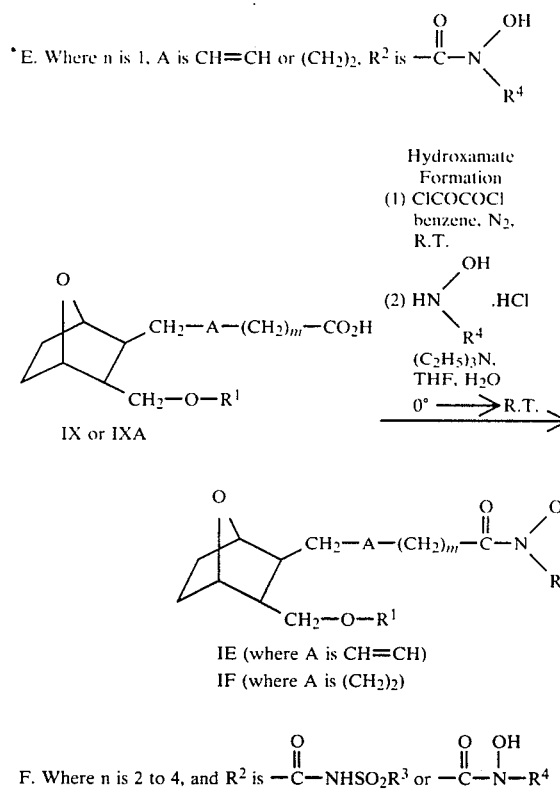

Hydroxamate Formation
(1) ClCOCOCl benzene, N₂, R.T.
(2) HN(OH)(R⁴)·HCl
(C₂H₅)₃N, THF, H₂O
0° → R.T.

IX or IXA

IE (where A is CH=CH)
IF (where A is (CH₂)₂)

F. Where n is 2 to 4, and R² is $-\overset{O}{\underset{\|}{C}}-\text{NHSO}_2\text{R}^3$ or $-\overset{O}{\underset{\|}{C}}-\text{N}(OH)(R^4)$

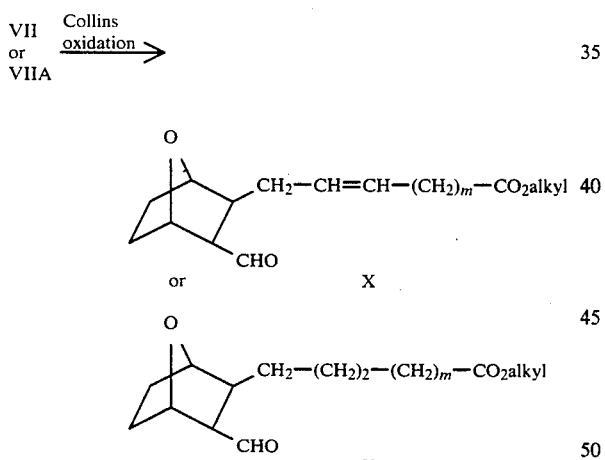

VII or VIIA — Collins oxidation →

X

XA

Wittig
(C₆H₅)₃P=CHOCH₃

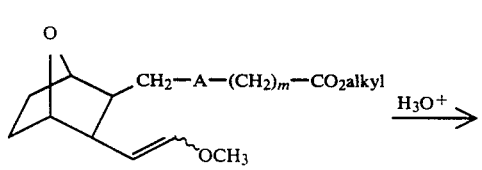

XI or XIA

H₃O⁺ →

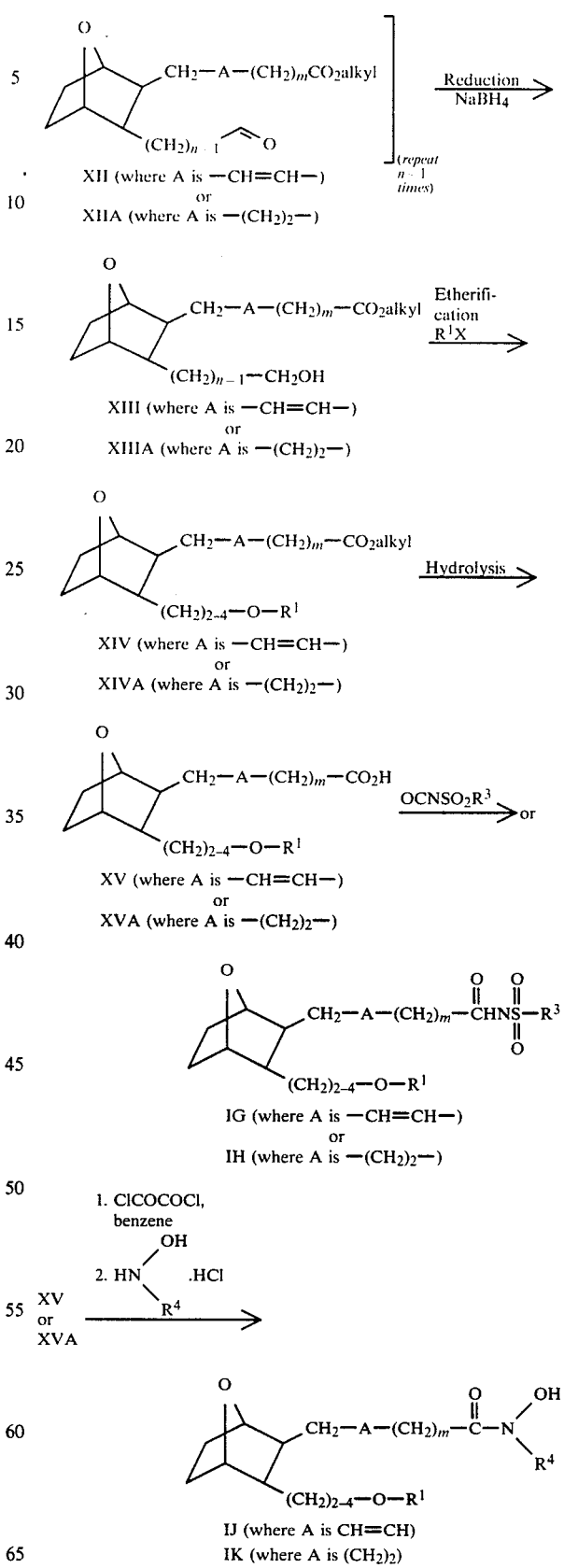

XII (where A is —CH=CH—)
or
XIIA (where A is —(CH₂)₂—)

Reduction
NaBH₄ →
(repeat n−1 times)

XIII (where A is —CH=CH—)
or
XIIIA (where A is —(CH₂)₂—)

Etherification
R¹X →

XIV (where A is —CH=CH—)
or
XIVA (where A is —(CH₂)₂—)

Hydrolysis →

XV (where A is —CH=CH—)
or
XVA (where A is —(CH₂)₂—)

OCNSO₂R³ → or

IG (where A is —CH=CH—)
or
IH (where A is —(CH₂)₂—)

1. ClCOCOCl, benzene
2. HN(OH)(R⁴)·HCl

XV or XVA →

IJ (where A is CH=CH)
IK (where A is (CH₂)₂)

Compounds of the invention wherein R² is

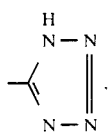

n is 1 and A is CH=CH, that is

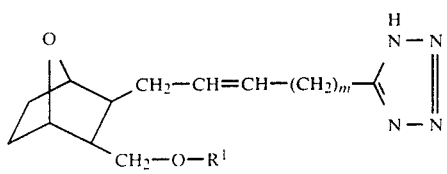
IA may be prepared as outlined in reaction sequence "A".

Diol compound II is employed as the starting material and is prepared by reacting the mesoanhydride A

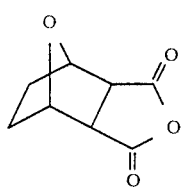
A (prepared as described in U.S. Pat. Nos. 4,143,054 and 4,220,594) with a reducing agent such as lithium aluminum hydride or diisobutylaluminum hydride in the presence of an inert organic solvent such as tetrahydrofuran, toluene or ether.

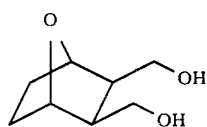
II

Diol II is etherified by reaction with a strong base such as sodium hydride in the presence of an inert solvent such as dimethylformamide and a compound of the structure B R¹X (wherein X is Br, Cl, OSO₂CH₃ or    B

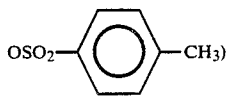

at temperatures of from about 80° to about 110° C., to form the ether III. Ether III is next chlorinated by reacting III with p-toluenesulfonyl chloride, lithium chloride and organic base such as pyridine to form IV. Compound IV is then reacted with sodium cyanide, in the presence of an inert solvent such as dimethylsulfoxide at 90° to 95° C. for 5 to 20 hours, to form compound V. Cyanide compound V is then treated with diisobutylaluminum hydride at reduced temperatures of from about −70° to about −78° C. under an inert atmosphere, such as argon, to form the aldehyde VI. The aldehyde VI is then treated with a tetrazole of the structure C

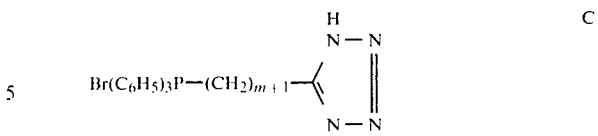

in the presence of strong base such as sodium hydride and an inert solvent such as dimethyl sulfoxide to form IA.

Compounds of formula I wherein A is (CH₂)$_n$, n is 1 and R is

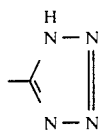

are prepared as shown in the reaction sequence "B" wherein compound IA is reduced by reaction with hydrogen in the presence of palladium on charcoal or similar catalyst to form compound IB.

In the reaction sequence identified as "C" and "D", where in Formula I n is 1, and R² is

the lower alkyl ester containing the hydroxymethyl group, that is, compound VII (where A is —CH=CH—, reaction sequence "C") or VIIA (where A is —(CH₂)₂, reaction sequence "D") (prepared as described in U.S. Pat. No. 4,143,054) is employed as the starting material. Thus, where A is —CH=CH—, compound VII is subjected to an etherification reaction, for example, by reacting compound A of the structure RX (wherein X is Cl, Br, I, OSO₂CH₃ or    A

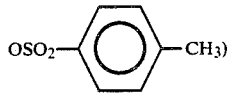

in the presence of a strong inorganic base such as KOH or NaOH, and an appropriate solvent to form ester VIII. To form the ester VIIIA (where A is (CH₂)₂), (Reaction sequence "D"), compound VII is reduced, for example with hydrogen over a palladium on carbon catalyst, to form hydroxymethyl compound VIIA (where A is (CH₂)₂) and compound VIIA is subjected to an etherification reaction as described above to form ester VIIIA (where A is (CH₂)₂). Thereafter, ester VIII or VIIIA is hydrolyzed, for example, by treatment with alkali metal hydroxide, to form the corresponding acid IX or IXA which in turn is reacted with compound D

OCNSO₂R³    D in the presence of triethylamine or similar base and inert organic solvent to form the corresponding compound of the invention IC or ID.

In carrying out the above etherification reaction, the hydroxymethyl compound VII or VIIA is employed in a molar ratio to the halide A, that is, VII or VIIA:A of within the range of from about 0.8:1 to about 1:5, employing a solvent such as xylene, tetrahydrofuran (THF), dimethylsulfoxide (DMSO) or dimethylformamide (DMF).

Where in RX, X is Br or Cl, a phase transfer etherification is employed in which case THF is used as the solvent and a phase transfer reagent such as Bu₄N-HSO₄, or (C₆H₅CH₂)(CH₃)₃NHSO₄ is employed.

In the reaction sequence identified as "E" where in Formula I, n is 1 and R² is

a solution of acid IX or IXA dissolved in an inert organic solvent such as benzene is treated with oxalyl chloride and the mixture is stirred at room temperature under nitrogen. The resulting acid chloride is dissolved in an inert organic solvent such as tetrahydrofuran and the so-formed solution is added dropwise into a cold solution of hydroxylamine hydrochloride E

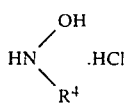

(employing a molar ratio of acid chloride:E of within the range of from about 0.3:1 to about 1:1 and preferably from about 0.5:1) and triethylamine in aqueous tetrahydrofuran to form the hydroxamate IE or IF

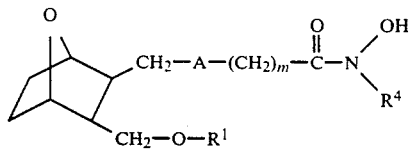

IE (where A is CH=CH)
IF (where A is (CH₂)₂)

In the reaction sequence identified as "F" where in Formula I n is 2 to 4, and R² is

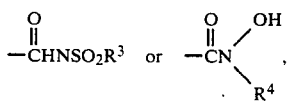

the starting lower alkyl ester containing the hydroxymethyl group, that is compound VII (prepared as described in U.S. Pat. No. 4,143,054), is used to form the aldehyde X (where A is —CH=CH—) or XA (where A is (CH₂)₂). Thus, to form aldehyde X where A is —CH=CH—, compound VII is subjected to a Collins oxidation, for example, by reacting VII with chromium trioxide in pyridine. To form the aldehyde XA (where A is (CH₂)₂), compound VII is reduced, for example with hydrogen over a palladium on carbon catalyst, to form hydroxymethyl compound VIIA (where A is (CH₂)₂) and compound VIIA is subjected to a Collins oxidation to form aldehyde XA (where A is (CH₂)₂).

The aldehyde X or XA is used to prepare aldehyde XII or XIIA (where n is 2-4) by carrying out a homologation sequence, such as a Wittig reaction with (C₆H₅)₃P=CHOMe followed by hydrolysis, (n−1) times. The aldehyde XII or XIIA (where n is 2-4) is thus carried on to compounds of this invention where n is 2-4, that is

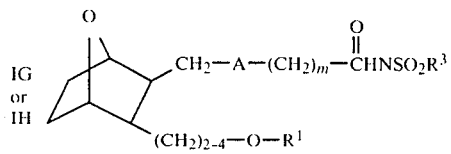

(IG where A is —CH=CH—)
(IH where A is (CH₂)₂)

by reducing aldehyde XII or XIIA employing a reducing agent such as sodium borohydride or sodium cyanoborohydride in a solvent such as methanol to form the alcohol ester XIII or XIIIA which is subjected to an etherification reaction as described above to form XIV or XIVA which is then treated with D or E as described above to form compounds of the invention.

Compounds of Formula I wherein R² is

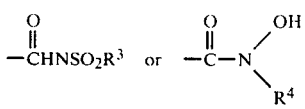

and R¹ is aryl such as phenyl or substituted phenyl may be prepared by reacting the alcohol VII or VIIA or XIII or XIIIA with triphenylphosphine and diethylazodicarboxylate in solution with an inert solvent such as THF, and thereafter without isolating any products, reacting the above reaction mixture with an aryl alcohol wherein the hydroxy group is directly attached to the aromatic ring, such as phenol or a substituted phenol, under an inert atmosphere, such as argon or nitrogen, to form the ester of the structure

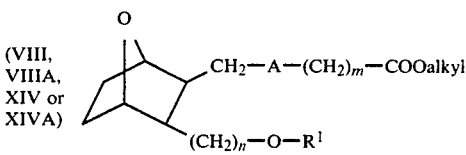

(VIII, VIIIA, XIV or XIVA)

wherein R¹ is phenyl or substituted phenyl, which is then treated with D or E as described above to form compounds of the invention.

The starting alcohol VII wherein (CH₂)ₘ is

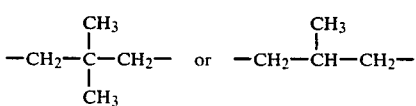

may be prepared as described in U.S. Pat. No. 4,143,054 or alternatively by subjecting the hemiacetal G

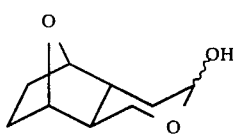

to a Wittig reaction by treating hemiacetal G with the reaction product of a carboxyalkyltriphenylphosphonium bromide H

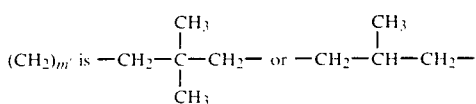

and potassium t-amylate and subsequently with diazomethane to form the alcohol VIIB

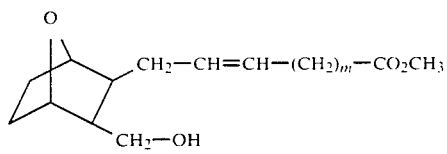

Alternatively, intermediates wherein

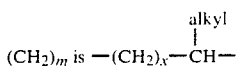

(wherein x is 1 to 7) may be prepared by simply reacting an ester XVI of the structure

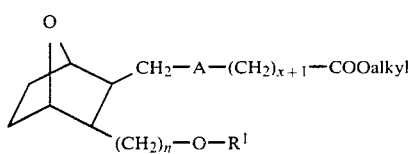

prepared as described hereinbefore with lithium diisopropylamide and then treating the reaction mixture with hexamethylphosphoramide and an alkyl halide J at reduced temperatures alkyl-Hal      J wherein Hal is I, Br, or Cl to form the ester XVII

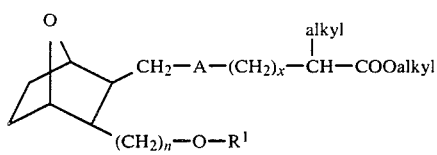

(wherein the above alkyls may be the same or different)

Intermediates wherein $(CH_2)_m$ is

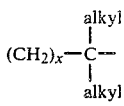

(wherein x is 1 to 7) may be prepared by reacting ester XVII with lithium diisopropylamide and then treating the reaction with an alkyl halide J at reduced temperatures to form the ester XVIII

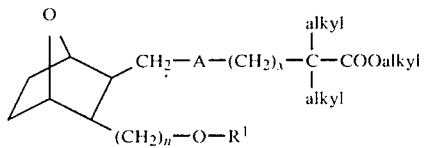

(wherein the various alkyls may be the same or different)

The ester VIII, VIIIA, XIV, XIVA, XVI, XVII or XVIII can be converted to the free acid, that is, to

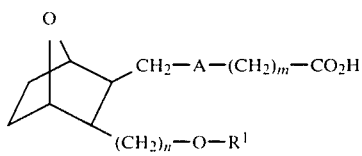

by treating the esters with an alkali metal hydroxide, such as lithium, sodium or potassium hydroxide to form the corresponding alkali metal salt, followed by neutralizing with an acid, such as dilute hydrochloric acid or oxalic acid to form the corresponding acid.

The compounds of this invention have four centers of asymmetry as indicated by the asterisks in formula I. However, it will be apparent that each of the formulae set out above which does not include asterisks still represents all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

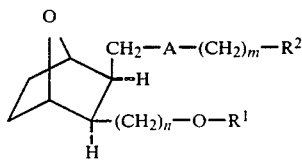

(cis-exo)

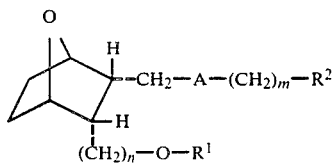

(cis-endo)

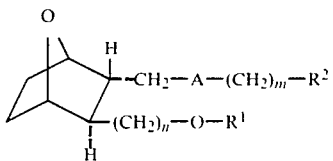

(trans)

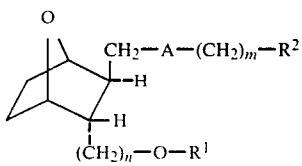

(trans)

The nucleus in each of the compounds of the invention is depicted as

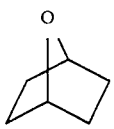

for matter of convenience; it will also be appreciated that the nucleus in the compounds of the invention may be depicted as

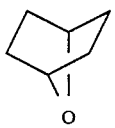

The compounds of this invention are cardiovascular agents useful as platelet aggregation inhibitors, such as in inhibiting arachidonic acid induced platelet aggregation, e.g., for treatment of thrombotic disease, such as coronary or cerebral thromboses or in inhibiting bronchoconstriction, such as associated with asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150: 165, 1965] and as antiinflammatory agents in mammals, as indicated by carrageenin-induced edema in the rat [Ref: Winter et al., J. Pharmacol., Exp. Ther. 141: 369, 1963]. They may be used to decrease joint swelling, tenderness, pain and stiffness in conditions such as rheumatoid arthritis.

The compounds of the invention may also be used in combination with a cyclic AMP phosphodiesterase (PDE) inhibitor such as theophylline or papaverine in the preparation of and to prolong storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1β,2α(Z),3α,4β]-5-[6-[3-[(Hexyloxy)methyl]-7-oxabicyclo[2.2.1]hept-2-yl]-4-hexenyl]-1H-tetrazole A. (1α,2β,3β,4α)-cis-exo-7-oxabicyclo[2.2.1]heptane-2,3-dimethanol To a suspension of 11.4 g lithium aluminum hydride (300 mmole, 1.6 eq.) in 400 ml of dry THF at 0° C. was added dropwise a solution of 32 g cis-exo-hexahydro-4,7-epoxyisobenzofuran-1,3-dione (mesoanhydride) (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

B. (1α,2β,3β,4α)-3-[(Hexyloxy)methyl]-7-oxabicyclo[2.2.1]heptane-2-methanol

A suspension of 50% sodium hydride (16.7 g or 0.35 mole; prewashed with ether) in dry dimethylformamide (350 ml) was cooled down to 0° under $N_2$ and treated dropwise with a solution of the Part A diol (50 g; 0.316 mole) in dry dimethylformamide (150 ml). The reaction mixture was stirred at 0° for 30 minutes and at room temperature for 30 minutes after which n-hexylbromide (70.3 g; 0.42 mmole) was added. The mixture was then stirred at room temperature for 15 minutes at 120° (oil bath) for 15 hours, cooled and quenched with 25% ammonium chloride solution (300 ml). The resulting suspension was extracted 3 times with ether (1.0 liter), the organic extracts were dried (anhydrous $MgSO_4$), filtered and evaporated to a syrup. Yield: 90.0 g.

The crude product mixture was chromatographed (gravity) on a silica gel column (Woelm; 1.2 kg), eluting the column with EtOAc-hexane (1:4, 24.3 liters). The desired fractions were combined and evaporated to give 26.94 g of homogeneous (tlc) compound. An additional 28.7 g of the title alcohol compound containing a trace of another component was obtained from other fractions giving a total yield of 72.6%. An analytical sample was obtained by distilling 1.0 g of the single spot material on a Buchi GKR-50 apparatus, (Temperature 225°; 0.4 mm).

$^1$H-NMR (270 MHz, CDCl$_3$): δ 0.89 (t, 3H, J=~8, H$_{21}$); 1.29–1.7 (m, 12H); 2.2 (m, 2H, J=~4, H$_8$+H$_{13}$); 3.3–3.80 (m, 7H, —, H$_7$, H$_{14}$+H$_{16}$); 4.23 (d, 1H, J=~2, H$_9$); 4.29 (d, 1H, J=~2, H$_{12}$).

Anal Calcd for C$_{14}$H$_{26}$O$_3$: C, 69.38; H, 10.81. Found: C, 69.36; H, 10.60.

C. (1α,2β,3β,4α)-2-Chloromethyl-3-(hexyloxy)methyl-7-oxabicyclo[2.2.1]heptane 5.0 g (20.6 mole) of (1α,2β,3β,4α)-3-(hexyloxy)methyl-7-oxabicyclo[2.2.1]-heptane-2-methanol (from Part B), 4.73 g (24.8 mmole of 1.2 eq.) of p-toluenesulfonylchloride, 873 mg (20.6 mmole) of lithium chloride and 3.3 ml of dry pyridine were stirred together in dichloromethane (15 ml) at room temperature under nitrogen for 24 hours. The reaction mixture was partitioned between ether (250 ml) and saturated sodium chloride solution (20 ml). The aqueous phase was re-extracted with ether (250 ml), the combined organic extracts were dried (anhydrous MgSO$_4$), filtered and the clear filtrate was evaporated down to a syrup. Yield: 5.3 g.

The crude product mixture was flash chromatographed on a silica gel column (LPS-1), eluting the column with Et$_2$O:hexane (1:9, 6.0 liters) and Et$_2$O:hexane (1:1; 6.0 liters). The fractions containing the desired product were combined and evaporated down to give 3.35 g (62.4%) of the title chloro compound as a homogeneous (tlc) oil with consistent H$^1$ and C$^{13}$ spectral data.

D. (1α,2β,3β,4α)-2-Cyanomethyl-3-(hexyloxy)methyl-7-oxabicyclo-[2.2.1]-heptane

A solution of Part C chloro compound (3.35 g; 12.8 mmole) and sodium cyanide (1.29 g; 2.05 eq.) in dry dimethylsulfoxide (4.6 ml) was heated at 90°–95° (oil bath) under argon for 19 hours with stirring. The mixture was cooled to room temperature, diluted with water (12 ml) and extracted twice with ether (75 ml). The organic extracts were dried (anhydrous MgSO$_4$), filtered and the clear filtrate concentrated in vacuo to a light yellow oil (3.18 g).

This oil was flash chromatographed on a silica gel column (LPS-1), eluting the column with Et$_2$O:hexane (1:2, 7.5 liters). The desired fractions were combined and concentrated to give 3.06 g (95%) of the title cyano compound as a homogeneous (tlc) light yellow oil with consistent H$^1$ and C$^{13}$-NMR spectral data.

E. (1α,2β,3β,4α)-3-(Hexyloxy)methyl-7-oxabicyclo[2.2.1]heptyl-2-acetaldehyde 1.5 g (5.97 mmole) of the Part D cyano compound was dissolved in dry toluene (7.0 ml), cooled, stirred in a bath at −78° (Dry ice-acetone) under argon, and treated dropwise with 5.4 ml of diisobutylaluminum hydride (25% by wt. in toluene; 9.49 mmole). After 4.0 hours, the mixture was quenched at −78° with 25% NH$_4$Cl (6.0 ml), stirred for 30 minutes, warmed to about 0°, acidified with 1N HCl (16 ml), and stirred for about 30 minutes. The mixture was then extracted twice with dichloromethane (50 ml), the organic extracts were washed with saturated sodium chloride solution (20 ml), dried (anhydrous MgSO$_4$), filtered and concentrated in vacuo to give 1.45 g (95.4%) of the title aldehyde as a homogeneous (tlc) yellow oil with consistent H$^1$ and C$^{13}$-NMR spectral data.

F. [1α,2β(Z),3β,4α]-5-[6-[3-[(Hexyloxy)methyl]-7-oxabicyclo[2.2.1]hept-2-yl]-4-hexenyl]-1H-tetrazole Sodium hydride (72 mg, 1.5 mmole of a 50% dispersion in mineral oil) in a flask was washed with several portions of n-hexane to remove the mineral oil. Dry dimethylsulfoxide (1.5 ml) was introduced via a syringe and the mixture was heated in a bath at 75°–80° under nitrogen for about 30 minutes (until the evaluation of hydrogen ceased). The resulting solution was cooled in an ice-water bath and (4-tetrazolo)butyltriphenylphosphonium bromide (374 mg, 0.8 mmole), (prepared as described by T. K. Schaff and H. J. Hess, J. Med. Chem., 22, 1340 (1979)) in 1.5 ml of warm dry dimethyl sulfoxide was added. The resulting dark red solution was stirred at room temperature for 15 minutes. To this ylide solution was added a solution of 127.2 mg (0.5 mmole) of Part E ether aldehyde in 1.0 ml of dry dimethylsulfoxide and stirred at room temperature under nitrogen for 3 hours. The reaction mixture was then poured into ice water containing ethyl acetate (100 ml). The aqueous layer was acidified with 10% HCl, the organic layer was separated, and the acidified aqueous layer extracted with ethyl acetate (3×50 ml). The combined organic extracts were dried over anhydrous MgSO$_4$ and concentrated in vacuo to give 200 mg of crude product. This was chromatographed on a silica gel (50 g, Baker, 60–200 mesh) column, eluting successively with ethyl acetate-hexane (35:65) and ethyl acetate to give 185 mg (51%) of the homogeneous (tlc) analytical specimen of the title tetrazole with consistent spectral data.

Anal Calcd for C$_{20}$H$_{34}$N$_4$O$_2$: C, 66.26; H, 9.45; N, 15.46. Found: C, 66.07; H, 9.35; N, 15.25.

H$^1$-NMR Spectrum (FX 270, CDCl$_3$): δ 0.86 (t, 3H, J=~8.0, H$_{21}$); 3.02 (m, 2H, H$_2$); 3.48 (m, 4H, H$_{14}$+H$_{16}$); 4.40 (d, 2H, J=~4.0, H$_9$); 4.60 (d, 2H, J=~4.0, H$_{12}$); 5.42 (m, 2H, H$_5$+H$_6$).

EXAMPLE 2

[1R-[1α,2β(Z),3β,4α]]-7-[3-[(Hexyloxy)methyl]-7-oxabicyclo[2.2.1]hept-2-yl]-N-(phenylsulfonyl)-5-heptenamide A. [3aR-[1-(1R,2S,5R),3aα,4α,7α,7aα]]-Octahydro-1-[[5-methyl-2-(1-methylethyl)cyclohexyl]oxy]-4,7-epoxyisobenzofuran A solution of (exo)-octahydro-4,7-epoxyisobenzofuran-1-ol prepared as described in U.S. Pat. No. 4,143,054 (21 g, 0.13 mole), levo-menthol (21 g, 0.13 mole) and p-toluenesulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10 g of [3aR-[1-(1R,2S-5R),3aα,4α,7α,7aα]]-octahydro-1-[[5-methyl-2-(1-methylethyl)cyclohexyl]oxy]-4,7-epoxyisobenzofuran, m.p. 109°–111° C.

B. [3aS-(3aα,4α,7α,7aα)]-Octahydro-1-benzyloxy-4,7-epoxyisobenzofuran

A solution of [3aR-[1-(1R,2S,5R),3aα,4α,7α,7aα]]-octahydro-1-[[5-methyl-2-(1-methylethyl)cyclohexyl]oxy]-4,7-epoxy-isobenzofuran (from Part A) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of title compound as an oil.

TLC: silica gel; hexane/ether (1:1), $R_f$=0.25; vanillin spray and heat.

C. [3aS-(3aα,4α,7α,7aα)]-Octahydro-4,7-epoxyisobenzofuran-1-ol

A mixture of title B compound (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C.

$[\alpha]_D = -44°$ $[\alpha]^{Hg}{}_{365} = -122°$ (c=10 mg/ml MeOH)

TLC: silica gel; ethyl acetate/dichloromethane (1:1), $R_f$=0.2; vanillin spray and heat.

D. [1R-(1α,2β,3β,4α)]-3-(Hydroxymethyl)-2-(2-methoxyethenyl)-7-oxabicyclo[2.2.1]heptane A slurry of methoxymethyltriphenylphosphonium chloride (28.1 g, 0.082 mole) in toluene (700 ml) was treated with a solution of lithium diisopropylamide [prepared from 1.6M n-butyl lithium (51 ml, 0.082 mole) and diisopropylamine (14.25 ml, 0.10 mole) in pentane] in tetrahydrofuran (20 ml). The mixture was stirred at room temperature for 30 minutes then treated with title C compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether two yield the desired title B product contaminated with phosphine oxide. This product was distilled in vacuo to yield 3 g of title D compound, b.p. 90° C./0.01 mm.

$[\alpha]_D = +44°$ $[\alpha]^{Hg}{}_{365} = +138°$ c=11 mg/ml MeOH

TLC: silica gel; ethyl acetate/dichloromethane (1:1); $R_f$=0.2; vanillin spray and heat.

E. [4aS-(4aα,5α,8α,8aα)]-Octahydro-5,8-epoxy-(1H)-benzopyran-3-ol

A solution of title D compound (3 g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title E compound, m.p. 104°-105° C.

$[\alpha]_D = +27.2°$ $[\alpha]^{Hg}{}_{365} = 0$ (c=7.9 mg/ml MeOH)

F. [1R-[1α,2β(5Z),3β,4α]]-7-[3-(Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes, then treated with title E compound (2.4 g, 0.0141 mole). The reaction mixtue was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title compound.

$[\alpha]_D = +11.2°$ $[\alpha]^{Hg}{}_{365} = 0$ c=16.9 mg/ml MeOH

TLC: silica gel; ether; $R_f$=0.4; vanillin spray and heat.

G. [1R-[1α,2β(Z),3β,4α]]-7-[3-[(Hexyloxy)methyl]-7-oxabicyclo[2.2.1]hept-2-yl]-5-heptenoic acid, hexyl ester A mixture of powdered KOH (0.93 g) in 25 ml of dry xylene was heated to reflux under argon atmosphere and 12 ml of xylene was removed by distillation. To this mixture was added a solution of 500 mg (1.86 mmol) of title F alcohol methyl ester in 16 ml of dry xylene. The volume of the reaction mixture was reduced 12 ml by distillative removal of xylene. To the reaction mixture was then added a solution of 1.68 g (9.30 mmol) hexylmesylate in 16 ml of dry xylene. This mixture was refluxed for 1 hour and 15 minutes. The cooled reaction mixture was diluted with 100 ml of saturated NaHCO$_3$ solution and extracted with CH$_2$Cl$_2$ (3×100 ml). The combined CH$_2$Cl$_2$ extracts were washed with brine (1×200 ml), dried (MgSO$_4$), filtered and concentrated in vacuo. Purification was effected by flash chromatography on 46 g of silica gel 60 using hexane:ethane (5:1) as eluant. This gave 0.62 g of title hexyl ester (79%) as a colorless oil. TLC: silica gel, 2% CH$_3$OH/CH$_2$Cl$_2$, $R_f$ 0.80, iodine. This reaction can also be accomplished by simultaneous addition of the mesylate and alcohol ester with similar results.

H. 1R-[1α,2β(Z),3β,4α]]-7-[3-[(Hexyloxy)methyl]-7-oxabicyclo[2.2.1]hept-2-yl]-5-heptenoic acid To a stirred solution of 517 mg (1.12 mmol) of Part G hexyl ester, 55 ml of distilled THF, 4.40 ml of $CH_3OH$ and 7.20 ml of $H_2O$ under argon was added 13.50 ml of 1N aqueous lithium hydroxide solution. This mixture was purged with argon vigorously for 30 minutes and stirred at room temperature for 15 hours. The reaction mixture was acidified to pH 3 by the addition of 1N aqueous HCl solution. The resulting solution was poured into 120 ml of saturated NaCl solution and was saturated with solid NaCl. The aqueous layer was extracted with EtOAc (4×150 ml). The combined EtOAc extracts were dried ($MgSO_4$), filtered and concentrated in vacuo. This was chromatographed on 40 g of silica gel 60 using 4% $CH_3OH$ in $CH_2Cl_2$ as eluant to give the desired product contaminated with a small amount of hexyl alcohol. The product was pumped under high vacuum for ~60 hours at room temperature to give 350 mg (85%) of pure title acid. TLC: silica gel, 4% $CH_3OH/CH_2Cl_2$, $R_f$=0.42, iodine.

$[\alpha]_D = +5.2°$ ($CHCl_3$)

Anal Calcd for $C_{20}H_{34}O_4$: C, 70.92; H, 10.12. Found: C, 70.66; H, 9.99.

I. [1R-[1α,2β(Z),3β,4α]]-7-[3-[(Hexyloxy)methyl]-7-oxabicyclo[2.2.1]hept-2-yl]-N-(phenylsulfonyl)-5-heptenamide A solution of 300 mg (0.866 mmole) of Part H acid, 0.24 ml (1.77 mmole) of benzenesulfonyl isocyanate and 0.25 ml (1.77 mmole) of triethylamine in 10 ml of dry tetrahydrofuran was stirred at room temperature under nitrogen for 2.5 hours. The resulting reaction mixture was diluted with ethyl acetate (50 ml), washed successively with saturated $NH_4Cl$ solution (25 ml), water (25 ml) and brine (25 ml), dried over anhydrous $MgSO_4$ and concentrated in vacuo to give an oil. This was flash-chromatographed on a silica gel (200 g, LPS-1) column, eluting with methanol-dichloromethane (2:98) to give 195 mg (46%) of the homogeneous (tlc) analytical specimen of the title compound with consistent IR, MS, $H^1$-NMR and $C^{13}$-NMR data; $[\alpha]_D^{20} = (-)3.1°$ (c=0.65; $CHCl_3$).

Anal Calcd for $C_{26}H_{39}NO_5S$: C, 65.38; H, 8.23; N, 2.93; S, 6.71. Found: C, 65.36; H, 8.30; N, 3.01; S, 6.84.

$H^1$-NMR Spectrum (FX 270, $CDCl_3$): δ0.89 (t, 3H, J= ~8.0, $H_{21}$); 2.25 (t, 2H, $H_2$); 3.40 (m, 4H, $H_{14}+H_{16}$); 4.28 (d, 1H, J= ~4.0, $H_9$); 4.52 (d, 1H, J= ~4.0, $H_{12}$); 5.30 (narrow m, 2H, $H_5+H_6$); 7.52 (dd, 2H, J= ~8.0, $H_{24}+H_{26}$); 7.61 (dd, 1H, J= ~8.0, $H_{25}$); 8.07 (d, 2H, J= ~8.0, $H_{23}+H_{27}$); 9.80 (broad, 1H, NH).

EXAMPLE 3

[1R-[1α,2β(Z),3β,4α]]-7-[3-[(Hexyloxy)methyl]-N-(methylsulfonyl)-7-oxabicyclo[2.2.1]hept-2-yl]-5-heptenamide A solution of 280 mg (0.827 mmole) of [1R-[1α,2β(Z),3β,4α]]-7-[3-[(hexyloxy)methyl]-7-oxabicyclo[2.2.1]hept-2-yl]-5-heptenoic acid (prepared as described in Example 2, Parts A–H), 450 mg (3.72 mmole) of methylsulfonyl isocyanate (prepared according to W. H. Daly and H. J. Holle, J. Org. Chem., 39, 1597 (1974)) and 0.52 ml (3.72 mmole) of triethylamine in 8 ml of dry tetrahydrofuran was stirred at room temperature under nitrogen for 3 hours. The resulting reaction mixture was diluted with ethyl acetate (50 ml), washed successively with saturated $NH_4Cl$ solution (20 ml), water (20 ml) and brine (20 ml), dried over anhydrous $MgSO_4$ and concentrated in vacuo to give an oil. This was chromatographed on a 60 g silica gel column, eluting successively with ethyl acetate-hexane (1:4 and 1:1) and ethyl acetate to give, after drying in vacuo, 130 mg (37.8%) of the homogeneous (tlc) analytical specimen of the title compound with consistent IR, MS, $^1$H-NMR and $C^{13}$-NMR data and $[\alpha]_D^{20} = -75°$ (c=0.65, $CHCl_3$).

Anal Calcd for $C_{21}H_{37}NO_5S$: C, 60.69; H, 8.98; N, 3.37; S, 7.72. Found: C, 60.66; H, 9.04; N, 3.34; S. 7.69.

$^1$H-NMR Spectrum (FX270, $CDCl_3$): δ0.90 (t, 3H, J= ~8, $H_{21}$); 2.31 (m, 2H, $H_2$); 3.30 (s, 3H, $H_{22}$); 3.40 (m, 4H, $H_{14}+H_{16}$); 4.29 (d, 1H, J= ~4, $H_9$); 4.49 (d, 1H, J= ~4, $H_{12}$); 5.39 (narrow m, 2H, $H_5+H_6$); 9.63 (broad, 1H, NH).

EXAMPLE 4

(1β,2α,3α,4β)-5-[6-[3-[(Hexyloxy)methyl]-7-oxabicyclo[2.2.1]hept-2-yl]heptyl]-1H-tetrazole To 3.0 mmol of the [1β,2α(Z),-3α,4β]-5-[6-[3-(hexyloxy)methyl]-7-oxabicyclo[2.2.1]hept-2-yl]-4-hexenyl]-1H-tetrazole as prepared in Example 1, dissolved in 120 ml of ethyl acetate is added, under an argon atmosphere, 160 mg of 5% Pd on carbon. The argon atmosphere is exchanged for a slight positive pressure of hydrogen and the reaction is stirred for 8 hours at 25°, filtered through a celite plug and evaporated to provide the title compound.

EXAMPLE 5

(1α,2β,3β,4α)-5-[6-[3-[(Hexyloxy)methyl]-7-oxabicyclo[2.2.1]hept-2-yl]-N-(phenylsulfonyl)heptaneamide A. (1β,2α,3α,4β)-7-[3-[(Hydroxy)methyl]-7-oxabicyclo[2.2.1]hept-2-yl]heptanoic acid, methyl ester To 800 mg (3.0 mmole) of the [1α,2β(5Z),3β,4α]-7-[3-(hydroxymethyl)-7-oxabicyclo[2.2.1]hept-2-yl]-5-heptenoic acid, methyl ester as prepared in Example 1, Part F, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. (1α,2β,3β,4α)-5-[6-[3-[(Hexyloxy)methyl]-7-oxabicyclo[2.2.1]hept-2-yl]-N-(phenylsulfonyl)heptaneamide Following the procedure of Example 2 except substituting the Part A alcohol-ester for the Example 1F alcohol ester, the title product is obtained.

EXAMPLE 6

[1α,2β(5Z),3β,4α]-7-[3-[(Phenyloxy)methyl]-7-oxabicyclo[2.2.1]hept-2-yl]-N-(phenylsulfonyl)-5-heptenamide (a) Phenol (1 mmol) is added to a solution of triphenylphosphine (1 mmol), diethylazodicarboxylate (1 mmol) and title F alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1α,2β(5Z),-3β,4α]-7-[3-[(phenyloxy)methyl]-7- oxabicyclo[2.2.1]hept-2-yl]-5-heptenoic acid, methyl ester.

(b) Following the procedure as set out in Example 2, the ester from part (a) is converted to the title compound.

EXAMPLE 7

[1β,2α(Z),3α,4β]-5-[6-[3-[(Benzyloxy)methyl]-7-oxabicyclo[2.2.1]hept-2-yl]-4-hexenyl]-1H-tetrazole Following the procedure of Example 1 except substituting benzyl bromide for n-hexyl bromide, the title compound is obtained.

EXAMPLE 8

[1β,2α(Z),3α,4β]-5-[6-[3-[(Cyclohexyloxy)methyl]-7-oxabicyclo[2.2.1]hept-2-yl]-4-hexenyl]-1H-tetrazole Following the procedure of Example 1 except substituting cyclohexyl bromide for n-hexyl bromide, the title compound is obtained.

EXAMPLE 9

[1β,2α(Z),3α,4β]-5-[6-[3-[(Propoxy)methyl]-7-oxabicyclo[2.2.1]hept-2-yl]-4-hexenyl]-1H-tetrazole Following the procedure of Example 1 except substituting propyl bromide for n-hexyl bromide, the title compound is obtained.

EXAMPLE 10

[1β,2α(Z),3α,4β]-5-[6-[3-[(Methoxy)methyl]-7-oxabicyclo[2.2.1]hept-2-yl]-4-hexenyl]-1H-tetrazole Following the procedure of Example 1 except substituting methyl bromide for n-hexyl bromide, the title compound is obtained.

EXAMPLE 11

[1β,2α(Z),3α,4β]-5-[6-[3-[(Cycloheptyloxy)methyl]-7-oxabicyclo[2.2.1]hept-2-yl]-4-hexenyl]-1H-tetrazole Following the procedure of Example 1 except substituting cycloheptyl bromide for n-hexyl bromide, the title compound is obtained.

EXAMPLE 12

[1β,2α(Z),3α,4β]-5-[8-[3-[(Benzyloxy)methyl]-7-oxabicyclo[2.2.1]hept-2-yl]-6-octenyl]-1H-tetrazole Following the procedure of Example 1 except substituting benzyl bromide for n-hexyl bromide and (6-tetrazolohexyl)triphenylphosphonium bromide for (4-tetrazolobutyl)triphenylphosphonium bromide, the title compound is obtained.

EXAMPLE 13

[1β,2α(Z),3α,4β]-5-[5-[3-[(Cyclopentylmethyloxy)methyl]-7-oxabicyclo[2.2.1]hept-2-yl]-3-pentenyl]-1H-tetrazole Following the procedure of Example 1 except substituting cyclopentylmethyl bromide for n-hexyl bromide and (3-tetrazolopropyl)triphenylphosphonium bromide for (4-tetrazolobutyl)triphenylphosphonium bromide, the title compound is obtained.

EXAMPLE 14

[1β,2α(Z),3α,4β]-5-[4-[3-[(Cyclohexyloxy)methyl]-7-oxabicyclo[2.2.1]hept-2-yl]-2-butenyl]-1H-tetrazole Following the procedure of Example 1 except substituting cyclohexyl bromide for n-hexyl bromide and (2-tetrazoloethyl)triphenylphosphonium bromide for (4-tetrazolobutyl)triphenylphosphonium bromide, the title compound is obtained.

EXAMPLE 15

[1β,2α(Z),3α,4β]-5-[7-[3-[(Propoxy)methyl]-7-oxabicyclo[2.2.1]hept-2-yl]-5-heptenyl]-1H-tetrazole Following the procedure of Example 1 except substituting propyl bromide for n-hexyl bromide and (5-tetrazolopentyl)triphenylphosphonium bromide for (4-tetrazolobutyl)triphenylphosphonium bromide, the title compound is obtained.

EXAMPLE 16

(1β,2α,3α,4β)-5-[3-[3-[(Methoxy)methyl]-7-oxabicyclo[2.2.1]hept-2-yl]propyl]-1H-tetrazole Following the procedure of Examples 1 and 4 except substituting methyl bromide for n-hexyl bromide and (1-tetrazolomethyl)triphenylphosphonium bromide for (4-tetrazolobutyl)triphenylphosphonium bromide, the title compound is obtained.

EXAMPLE 17

(1β,2α,3α,4β)-5-[4-[3-[(Cyclohexyloxy)methyl]-7-oxabicyclo[2.2.1]hept-2-yl]butyl]-1H-tetrazole Following the procedure of Examples 1 and 4 except substituting cyclohexyl bromide for n-hexyl bromide and (2-tetrazoloethyl)triphenylphosphonium bromide for (4-tetrazolobutyl)triphenylphosphonium bromide, the title compound is obtained.

EXAMPLE 18

(1β,2α,3α,4β)-5-[7-[3-[(Benzyloxy)methyl]-7-oxabicyclo[2.2.1]hept-2-yl]heptyl]-1H-tetrazole Following the procedure of Examples 1 and 4 except substituting benzyl bromide for n-hexyl bromide and (5-tetrazolopentyl)triphenylphosphonium bromide for (4-tetrazolobutyl)triphenylphosphonium bromide, the title compound is obtained.

EXAMPLE 19

(1β,2α,3α,4β)-5-[9-[3-[(Cyclohexylmethyloxy)methyl]-7-oxabicyclo[2.2.1]hept-2-yl]nonyl]-1H-tetrazole Following the procedure of Examples 1 and 4 except substituting cyclohexylmethyl bromide for n-hexyl bromide and (7-tetrazoloheptyl)triphenylphosphonium bromide for (4-tetrazolobutyl)triphenylphosphonium bromide, the title compound is obtained.

EXAMPLE 20

(1β,2α,3α,4β)-5-[8-[3-[(Phenyloxy)methyl]-7-oxabicyclo[2.2.1]hept-2-yl]octyl]-1H-tetrazole Following the procedure of Examples 1, 4 and 6 except substituting (6-tetrazolohexyl)triphenylphosphonium bromide for (4-tetrazolobutyl)triphenylphosphonium bromide, the title compound is obtained.

EXAMPLE 21

[1R-[1α,2β(Z),3β,4α]]-7-[3-[(Benzyloxy)methyl]-7-oxabicyclo[2.2.1]hept-2-yl]-N-(benzylsulfonyl)-5-heptenamide Following the procedure of Example 2 except substituting benzyl mesylate for hexyl mesylate and substituting benzylsulfonyl isocyanate for benzenesulfonyl isocyanate, the title compound is obtained.

EXAMPLE 22

[1R-[1α,2β(Z),3β,4α]]-7-[3-[(Cyclopropyloxy)methyl]-7-oxabicyclo[2.2.1]hept-2-yl]-N-(octylsulfonyl)-5-heptenamide Following the procedure of Example 2 except substituting cyclopropyl mesylate for hexyl mesylate and substituting octylsulfonyl isocyanate for benzenesulfonyl isocyanate, the title compound is obtained.

EXAMPLE 23

[1R-[1α,2β(Z),3β,4α]]-7-[3-[(Cyclohexylethyloxy)methyl]-7-oxabicyclo[2.2.1]hept-2-yl]-N-(hexylsulfonyl)-5-heptenamide Following the procedure of Example 2 except substituting cyclohexylethyl mesylate for hexyl mesylate and substituting hexylsulfonyl isocyanate for benzenesulfonyl isocyanate, the title compound is obtained.

EXAMPLE 24

[1R-[1α,2β(Z),3β,4α]]-7-[3-[(Butyloxy)methyl]-7-oxabicyclo[2.2.1]hept-2-yl]-N-(ethylsulfonyl)-5-heptenamide Following the procedure of Example 2 except substituting butyl mesylate for hexyl mesylate and substituting ethylsulfonyl isocyanate for benzenesulfonyl isocyanate, the title compound is obtained.

EXAMPLE 25

[1R-[1α,2β(Z),3β,4α]]-7-[3-[(Phenyloxy)methyl]-7-oxabicyclo[2.2.1]hept-2-yl]-N-(benzylsulfonyl)-5-heptenamide Following the procedure of Examples 2 and 6 except substituting benzylsulfonyl isocyanate for benzenesulfonyl isocyanate, the title compound is obtained.

EXAMPLE 26

(1α,2β,3β,4α)-5-[6-[3-[(Benzyloxy)methyl]-7-oxabicyclo[2.2.1]hept-2-yl]-N-(benzylsulfonyl)heptaneamide Following the procedure of Examples 2 and 5 except substituting benzyl mesylate for hexyl mesylate and substituting benzylsulfonyl isocyanate for benzenesulfonyl isocyanate, the title compound is obtained.

EXAMPLE 27

(1α,2β,3β,4α)-5-[6-[3-[(Cyclohexyloxy)methyl]-7-oxabicyclo[2.2.1]hept-2-yl]-N-(benzylsulfonyl)heptaneamide Following the procedure of Examples 2 and 5 except substituting cyclohexyl mesylate for hexyl mesylate and substituting benzylsulfonyl isocyanate for benzenesulfonyl isocyanate, the title compound is obtained.

EXAMPLE 28

(1α,2β,3β,4α)-5-[6-[3-[(Phenyloxy)methyl]-7-oxabicyclo[2.2.1]hept-2-yl]-N-(octylsulfonyl)heptaneamide Following the procedure of Examples 2, 5 and 6 except substituting octylsulfonyl isocyanate for benzenesulfonyl isocyanate, the title compound is obtained.

EXAMPLE 29

(1α,2β,3β,4α)-5-[6-[3-[(Ethyloxy)methyl]-7-oxabicyclo[2.2.1]hept-2-yl]-N-(ethylsulfonyl)heptaneamide Following the procedure of Examples 2 and 5 except substituting ethyl mesylate for hexyl mesylate and substituting ethylsulfonyl isocyanate for benzenesulfonyl isocyanate, the title compound is obtained.

EXAMPLE 30

[1α,2β(Z),3β,4α]-7-[3-[2-(Hexyloxy)ethyl]-7-oxabicyclo[2.2.1]hept-2-yl]-N-(phenylsulfonyl)-5-heptenamide A. [1α,2β(Z),3β,4α]-7-[3-(2-Oxo)ethyl]-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride ((C₆H₅)₃P⁺—CH₂OCH₃Cl⁻) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1α,2β(Z),3β,4α]-7-[3-formyl-7-oxabicyclo[2.2.1]hept-2-yl]-5-heptenoic acid, methyl ester as prepared in U.S. Pat. No. 4,143,054, in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH₄Cl, and extracted with ether (4×200 ml). The combined ether phases were washed with NaCl saturated solution, and dried (MgSO₄) and concentrated to yield a yellow oil in a white crystalline solid (phosphine oxide). The white solid was triturated with EtOAc removed by filtration and the mother liquor was purified by chromatography on an LPS-1 silica column. The fractions obtained were (A) [1α,2β(Z),3β,4α]-7-[3-(2-oxo)ethyl-7-oxabicyclo[2.2.1-]hept-2-yl]-5-heptanoic acid, methyl ester, (B) [1α,2β(Z),3β,4α]-7-[3-(2-methoxy)ethendiyl]-7-oxabicyclo[2.2.1]hept-2-yl]-5-heptenoic acid, methyl ester, and (C) [1α,2β(Z),-3β,4α]-7-[3-(2,2-dimethoxy)ethyl-7-oxabicyclo[2.2.1]hept-2-yl]-5-heptenoic acid, methyl ester.

Compounds (B) and (C) are each treated with aqueous trifluoroacetic acid to convert each to compound (A).

B. [1α,2β(Z),3β,4α]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) was treated with NaBH₄ (0.19 g, 5 mmol) in an argon atmosphere at 0° C. After stirring at 0° C. for 1 hour, the reaction was quenched by addition of 2N HCl (to pH 2). The methanol was removed in vacuo and the reaction mixture was taken up in ether. The ether solution was washed with saturated KHCO₃, saturated NaCl and dried (MgSO₄). The ether was evaporated to yield the title B compound.

C. [1α,2β(Z),3β,4α]-7-[3-[2-(Hexyloxy)ethyl]-7-oxabicyclo[2.2.1]hept-2-yl]-5-heptenoic acid Following the procedure of Example 2 except substituting the above part B alcohol for the alcohol used in Example 1, Part G, the title compound is obtained.

EXAMPLE 31

(1α,2β,3β,4α)-7-[3-[2-(Hexyloxy)ethyl]-7-oxabicyclo[2.2.1]hept-2-yl]-N-(phenylsulfonyl)heptanamide Following the procedure of Example 30 except substituting (1α,2β,3β,4α)-7-[3-formyl-7-oxabicyclo[2.2.1]hept-2-yl]heptanoic acid, methyl ester for [1α,2β(Z),3β,4α]-7-[3-formyl-7-oxabicyclo[2.2.1]hept-2-yl]-5-heptenoic acid, methyl ester, the title compound is obtained.

EXAMPLE 32

[1α,2β(Z),3β,4α]-7-[3-[3-(Phenyloxy)propyl]-7-oxabicyclo[2.2.1]hept-2-yl]-N-(phenylsulfonyl)-5-heptenamide Following the procedure of Examples 5, 6 and 30 except substituting [1α,2β(Z),3β,4α]-7-[3-[2-(hydroxy)ethyl]-7-oxabicyclo[2.2.1]hept-2-yl]-5-heptenoic acid, methyl ester for [1α,2β(Z),3β,4α]-7-[3-(hydroxymethyl)-7-oxabicyclo[2.2.1]-hept-2-yl]-5-heptenoic acid, methyl ester, the title compound is obtained.

EXAMPLE 33

(1α,2β,3β,4α)-7-[3-[3-(Phenyloxy)propyl]-7-oxabicyclo[2.2.1]hept-2-yl]-N-(phenylsulfonyl)heptaneamide Following the procedure of Examples 5, 6 and 30 except substituting (1β,2α,3α,4β)-7-[3-[2-(hydroxy)ethyl]-7-oxabicyclo[2.2.1]hept-2-yl]heptanoic acid, methyl ester for [1β,2α(Z),3α,4β]-7-[3-(hydroxymethyl)-7-oxabicyclo[2.2.1]hept-2-yl]-5-heptenoic acid, methyl ester, the title compound is obtained.

EXAMPLE 34

[1α,2β(Z),3β,4α]-7-[3-[2-(Benzyloxy)ethyl]-7-oxabicyclo[2.2.1]hept-2-yl]-N-(phenylsulfonyl)-5-heptenamide Following the procedure of Example 30 except substituting benzyl mesylate for n-hexyl mesylate, the title compound is obtained.

EXAMPLE 35

[1α,2β(Z),3β,4α]-7-[3-[2-(Cyclohexyloxy)ethyl]-7-oxabicyclo[2.2.1]hept-2-yl]-N-(benzysulfonyl)-5-heptenamide Following the procedure of Example 30 except substituting cyclohexyl mesylate for hexyl mesylate and substituting benzyl sulfonyl isocyanate for benzenesulfonyl isocyanate, the title compound is obtained.

EXAMPLE 36

[1α,2β(Z),3β,4α]-7-[3-[2-(Pentyloxy)ethyl]-7-oxabicyclo[2.2.1]hept-2-yl]-N-(propylsulfonyl)-5-heptenamide Following the procedure of Example 30 except substituting pentyl mesylate for hexyl mesylate and substituting propylsulfonyl isocyanate for phenylsulfonyl isocyanate, the title compound is obtained.

EXAMPLE 37

[1α,2β(Z),3β,4α]-7-[3-[4-(Hexyloxy)butyl]-7-oxabicyclo[2.2.1]hept-2-yl]-N-(phenylsulfonyl)-5-heptenamide acid A. [1α,2β(Z),3β,4α]-7-[3-(3-Oxo)propyl-7-oxabicyclo[2.2.1]hept-2-yl]-5-heptenoic acid, methyl ester Following the procedure of Example 30, part A except substituting [1α,2β(Z),3β,4α]-7-[3-(2-oxo)-ethyl-7-oxabicyclo[2.2.1]hept-2-yl]-5-heptenoic acid, methyl ester for [1α,2β(Z),3β,4α]-7-[3-formyl-7-oxabicyclo[2.2.1]hept-2-yl]-5-heptenoic acid, methyl ester, the title A compound is obtained.

B. [1α,2β(Z),3β,4α]-7-[3-(4-Oxo)butyl-7-oxabicyclo[2.2.1]hept-2-yl]-5-heptenoic acid, methyl ester Following the procedure of Example 30, part A, except substituting the aldehyde from part A above, for [α,2β(Z),3β,4α]-7-[3-(2-Oxo)ethyl-7-oxabicyclo[2.2.1]hept-2-yl]-5-heptenoic acid, methyl ester, the title B aldehyde is obtained.

C. [1α,2β(Z),3β,4α]-7-[3-(4-Hydroxybutyl)-7-oxabicyclo[2.2.1]hept-2-yl]-5-heptenoic acid, methyl ester Following the procedure of Example 30, part B, except substituting the title B aldehyde for [1α,2β(Z),3β,-4α]-7-[3-(2-oxo)ethyl-7-oxabicyclo[2.2.1]hept-2-yl]-5-heptenoic acid, methyl ester, the title C alcohol is obtained.

D. [1α,2β(Z),3β,4α]-7-[3-[4-Hexyloxy)butyl]-7-oxabicyclo[2.2.1]hept-2-yl]-N-(phenylsulfonyl)-5-heptenamide Following the procedure of Example 2 except substituting the above part C alcohol for the alcohol used in Example 2, the title compound is obtained.

EXAMPLE 38

[1α,2β(Z),3β,4α]-7-[3-[4-(Cyclohexyloxy)butyl]-7-oxabicyclo[2.2.1]hept-2-yl]-N-(phenylsulfonyl)-5-heptenamide Following the procedure of Example 37 except substituting cyclohexyl mexylate for n-hexyl mesylate, the title compound is obtained.

EXAMPLE 39

[1α,2β(Z),3β,4α]-7-[3-[4-(Phenyloxy)butyl]-7-oxabicyclo[2.2.1]hept-2-yl]-N-(methylsulfonyl)-5-heptenamide Following the procedure of Examples 3, 6 and 37 except substituting [1α,2β(Z),3β,4α]-7-[3-(4-hydroxybutyl)-7-oxabicyclo[2.2.1]hept-2-yl]-5-heptenoic acid, methyl ester for [1α,2β(Z),3β,4α]-7-[3-(hydroxymethyl)-7-oxabicyclo[2.2.1]hept-2-yl]-5-heptenoic acid, methyl ester, the title compound is obtained.

EXAMPLE 40

[1α,2β(Z),3β,4α]-7-[3-[4-(Benzyloxy)butyl]-7-oxabicyclo[2.2.1]hept-2-yl]-N-(methylsulfonyl)-5-heptenamide Following the procedure of Examples 3 and 37 except substituting benzyl mesylate for n-hexyl mesylate, and substituting methyl sulfonyl isocyanate for benzenesulfonyl isocyanate, the title compound is obtained.

EXAMPLES 41 TO 50

Following the procedure of Examples 2, 3, 5 and 6 except substituting the hydroxymethyl compound, the RX compound and the OCNSO$_2$R$^3$ compound for the corresponding compounds, the product shown in Column IV below is obtained.

-continued

| | Col. I | | | Col. II | Col. III | | Col. IV | | | |
|---|---|---|---|---|---|---|---|---|---|---|
| Ex. No. | ![structure with CH2-A-(CH2)m-CO2CH3 and CH2OH on oxabicyclic] | A | (CH2)m | R¹Br R¹ | OCNSO2R³ R³ | R | ![structure with CH2-A-(CH2)m-CHNSO2R³ (C=O) and CH2-O-R on oxabicyclic] A | (CH2)m | R³ |
| 50. | | (CH2)2 | (CH2)6 | ⌬ | C2H5 | ⌬ | (CH2)2 | (CH2)6 | C2H5 |

EXAMPLE 51

[1R-[1α,2β(5Z),3β,4α]]-7-[3-[(Hexyloxy)methyl]-7-oxabicyclo[2.2.1]hept-2-yl]-N-hydroxy-N,2,2-trimethyl-5-heptenamide A.  [3aR-[1-(1R,2S,5R),3aα,4α,7α,7aα]]Octahydro-1-[[5-methyl-2-(1-methylethyl)cyclohexyl]oxy]-4,7-epoxyisobenzofuran A solution of (exo)-octahydro-4,7-epoxyisobenzofuran-1-ol prepared as described in U.S. Pat. No. 4,143,054 (21 g, 0.13 mole), levo-methanol (21 g, 0.13 mole) and p-toluenesulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10 g of [3aR-[1-(1R,2S,5R),3aα,4α,7α,7aα]]-octahydro-1-[[5-methyl-2-(1-methylethyl)cyclohexyl]oxy]-4,7-epoxyisobenzofuran, m.p. 109°–111° C.

B.  [3aS-(3aα,4α,7α,7aα)]-Octahydro-1-benzyloxy-4,7-epoxyisobenzofuran

A solution of [3aR-[1-(1R,2S,5R),3aα,4α,7α,7aα]]-octahydro-1-[[5-methyl-2-(1-methylethyl)cyclohexyl]oxy]-4,7-epoxy-isobenzofuran (from Part A) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of title compound as an oil.

TLC: silica gel; hexane/ether (1:1), $R_f$=0.25; vanillin spray and heat.

C.  [3aS-(3aα,4α,7α,7aα)]-Octahydro-4,7-epoxyisobenzofuran-1-ol

A mixture of title B compound (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C.

$[\alpha]_D$= −44° $[\alpha]^{Hg}{}_{365}$= −122° (c=10 mg/ml MeOH)

TLC: silica gel; ethyl acetate/dichloromethane (1:1), $R_f$=0.2; vanillin spray and heat.

D.  [1R-(1α,2β,3β,4α)]-3-(Hydroxymethyl)-2-(2-methoxyethenyl)-7-oxabicyclo[2.2.1]heptane A slurry of methoxymethyltriphenylphosphonium chloride (28.1 g, 0.082 mole) in toluene (700 ml) was treated with a solution of lithium diisopropylamide [prepared from 1.6M n-butyl lithium (51 ml, 0.082 mole) and diisopropylamine (14.25 ml, 0.10 mole) in pentane] in tetrahydrofuran (20 ml). The mixture was stirred at room temperature for 30 minutes then treated with title C compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether to yield the desired title B product contaminated with phosphine oxide. This product was distilled in vacuo to yield 3 g of title D compound, b.p. 90° C./0.01 mm.

$[\alpha]_D$= +44° $[\alpha]^{Hg}{}_{365}$= +138° (c=11 mg/ml MeOH)

TLC: silica gel; ethyl acetate/dichloromethane (1:1); $R_f$=0.2; vanillin spray and heat.

E.  [4aS-(4aα,5α,8α,8aα)]-Octahydro-5,8-epoxy-(1H)-benzopyran-3-ol

A solution of title D compound (3 g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title E compound, m.p. 104°–105° C.

$[\alpha]_D$= +27.2° $[\alpha]^{Hg}{}_{365}$=0 c=7.9 mg/ml MeOH

F.  [1R-[1α,2β(5Z), 3β,4α]]-7-[3-(Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes, then treated with title E compound (2.4 g, 0.0141 mole). The reaction mixture was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title compound.

$[\alpha]_D$= +11.2° $[\alpha]^{Hg}{}_{365}$=0 c=16.9 mg/ml MeOH

TLC: silica gel; ether; $R_f=0.4$; vanillin spray and heat.

G. [1R-[1α,2β(Z),3β,4α]]-7-[3-[(Hexyloxy)methyl]-7-oxabicyclo[2.2.1]hept-2-yl]-5-heptenoic acid, hexyl ester A mixture of powdered KOH (0.93 g) in 25 ml of dry xylene was heated to reflux under argon atmosphere and 12 ml of xylene was removed by distillation. To this mixture was added a solution of 500 mg (1.86 mmol) of title F alcohol methyl ester in 16 ml of dry xylene. The volume of the reaction mixture was reduced 12 ml by distillative removal of xylene. To the reaction mixture was then added a solution of 1.68 g (9.30 mmol) hexylmesylate in 16 ml of dry xylene. This mixture was refluxed for 1 hour and 15 minutes. The cooled reaction mixture was diluted with 100 ml of saturated $NaHCO_3$ solution and extracted with $CH_2Cl_2$ (3 × 100 ml). The combined $CH_2Cl_2$ extracts were washed with brine (1 × 200 ml), dried ($MgSO_4$), filtered and concentrated in vacuo. Purification was effected by flash chromatography on 46 g of silica gel 60 using hexane:ethane (5:1) as eluant. This gave 0.62 g of title hexyl ester (79%) as a colorless oil. TLC: silica gel, 2% $CH_3OH/CH_2Cl_2$, $R_f$: 0.80, iodine.

This conversion can also be accomplished in comparable yield by the simultaneous additon of mesylate and alcohol.

H. 1R-[1α,2β(Z),3β,4α]]-7-[3-[(Hexyloxy)methyl]-7-oxabicyclo[2.2.1]hept-2-yl]-5-heptenoic acid To a stirred solution of 517 mg (1.12 mmol) of Part G hexyl ester, 55 ml of distilled THF, 4.40 ml of $CH_3OH$ and 7.20 ml of $H_2O$ under argon was added 13.50 ml of 1N aqueous lithium hydroxide solution. This mixture was purged with argon vigorously for 30 minutes and stirred at room temperature for 15 hours. The reaction mixture was acidified to pH 3 by the addition of 1N aqueous HCl solution. The resulting solution was poured into 120 ml of saturated NaCl solution and was saturated with solid NaCl. The aqueous layer was extracted with EtOAc (4 × 150 ml). The combined EtOAc extracts were dried ($MgSO_4$), filtered and concentrated in vacuo. This was chromatographed on 40 g of silica gel 60 using 4% $CH_3OH$ in $CH_2Cl_2$ as eluant to give the desired product contaminated with a small amount of hexyl alcohol. The product was pumped under high vacuum for ~60 hours at room temperature to give 350 mg (85%) of pure title acid. TLC: silica gel, 4% $CH_3OH/CH_2Cl_2$, $R_f=0.42$, iodine.

$[\alpha]_D = +5.2°$ ($CHCl_3$)

Anal Calcd for $C_{20}H_{34}O_4$: C, 70.92; H, 10.12. Found: C, 70.66; H, 9.99.

I. [1R-[1α,2β(Z),3β,4α]]-7-[3-[(Hexyloxy)methyl]-7-oxabicyclo[2.2.1]hept-2-yl]-5-heptenoic acid, methyl ester

[1R-[1α,2β(Z),3β,4α]]-7-[3-[(Hexyloxy)methyl]-7-oxabicyclo[2.2.1]hept-2-yl]-5-heptenoic acid (1.35 g, 4 mmole, prepared as described in Part H) was dissolved in $Et_2O$ (~30 ml) and a moderate excess of a solution of diazomethane in $Et_2O$ was added. After 5 minutes, the excess diazomethane was destroyed by the addition of 2-3 drops of glacial acetic acid. After evaporation of the solvent the residue was flash-chromatographed on a column of silica gel (LP-1, 40 g) eluting the column with ether-hexane (15:85), with tlc monitoring of the fractions, to isolate slightly impure title ester (430 mg, 31%) and pure title ester (958 mg, 68%)[1] as oils with consistent IR, $H^1$-NMR and $C^{13}$-NMR and $[\alpha]_D^{25} + 5.47°$ (C, 2.01; $CHCl_3$). The total yield was 99%.

Anal Calcd for $C_{21}H_{36}O_4$: C, 71.55; H, 10.29. Found: C, 71.29; H, 10.37.

270 MHz $H^1$-NMR spectrum ($CDCl_3$): δ 0.9 (t, 3H, J=8.5, $CH_3$); 1.3 (s, 8 to 9H, $CH_2$); 2.03 (m, 5H, J=~9.0, $CH_2CH=$); 2.31 (t, 2H, J=8.5, $CH_2COO$); 3.33 (m, 4H, J=9.0, $CH_2O$); 4.66 (s, 3H, $COOCH_3$); 4.15 (d, 2H, J=~5.0, $H_9$); 4.38 (d, 2H, J=~5.0, $H_{12}$); 5.4 (m, 2H, J=~5.0, 14, $H_5$ and $H_6$).

1. The $H^1$-NMR spectrum showed the presence of 3.5 to 4% of the trans-double bond isomer.

J. [1R-[1α,2β(2(R,S),5Z),3β,4α]]-7-[3-[(Hexyloxy)methyl]-7-oxabicyclo[2.2.1]hept-2-yl]-2-methyl-5-heptenoic acid, methyl ester A solution of diisopropylamine (4.0 mmole, 404 mg) in dry THF (75ml) was cooled and stirred in a bath at −78° (Dry ice-acetone) under nitrogen and 1.7M butyllithium in hexane (3.0 mmole, 1.8 ml) was added. After 5 minutes, a solution of the Part I ester (3.0 mmole, 1.05 g) in dry THF (12 ml) was added dropwise in the course of 5 minutes. After another 15 minutes, hexamethyl phosphoric triamide (1.5 ml) and methyl iodide (neat, 12 mmole, 1.8 g) were added. After 1.5 hours, the solution was allowed to warm to room temperature in the course of about 30 minutes. The mixture was then poured into saturated brine (150 ml) and was extracted with ether (3 × 80 ml). The extracts were combined, washed with water, dried ($MgSO_4$ anhydrous) and evaporated to afford the crude product as an oil (1.0 g). On the basis of tlc, this was a mixture of essentially two compounds: title ester (major), and Part I ester (minor). In addition, minor, more polar impurities were present. This was subjected to a flash chromatography on a silica gel (LPS-1) column to isolate respectively, title ester (900 mg, 83%), and Part I ester (100 mg, 9.5%).

K. [1R-[1α,2β(Z),3β,4α]]-7-[3-[(Hexyloxy)methyl]-7-oxabicyclo[2.2.1]hept-2-yl]-2,2-dimethyl-5-heptenoic acid, methyl ester A solution of dry isopropylamine (2.0 mmole, 202 mg) in dry THF (12 ml) was cooled and stirred in a bath at −78° (Dry ice-acetone) under an atmosphere of nitrogen and 1.7M n-BuLi in hexane (1.8 mmole, 1.06 ml) was added. After 5.0 minutes, a solution of [1R-[1α,2β(2(R,S),5Z,3β,4α]]-7-[3-[(hexyloxy)methyl]-7-oxabicyclo[2.2.1]hept-2-yl]-2-methyl-5-heptenoic acid, methyl ester prepared as described in Part J (1.77 mmole, 650 mg) in dry THF (6.0 ml) was added in the course of 5 minutes. After 10 minutes, methyl iodide and hexamethyl phosphoric triamide (0.8 ml) (6.0 mmole, 850 mg) were added. After 1.5 hours, the solution was warmed to room temperature in the course of about 30 minutes. It was then added into 2% hydrochloric acid (75 ml) and was extracted with ether (3 × 40 ml). The extracts were combined, washed with water (2 × 20 ml), dried ($MgSO_4$ anhydrous) and evaporated to afford impure title methyl ester and an oil (640 mg, 95%). This was subjected to a flash chromatography on a silica gel (LPS-1) column to yield: title ester (640 mg, 95%). The title ester was homogeneous (tlc, $Et_2O$-hexane, 1:1) and its $H^1$ and $C^{13}$-NMR spectra were consistent with the structure.

L [1R-[1α,2β(Z),3β,4α]]-7-[3-[(Hexyloxy)methyl]-7-oxabicyclo[2.2.1]hept-2-yl]-2,2-dimethyl-5-heptenoic acid A solution of Part K ester (233 mg, 0.612 mmole) in THF (4.0 ml) was mixed with 1N LiOH (4.0 ml) and was stirred under an atmosphere of nitrogen for 24 hours. No hydrolysis was observed by tlc of an acidified (dil. HCl) aliquot. Therefore, solid LiOH-1H$_2$O (12 mmole, 504 mg) was added and the mixture was stirred under reflux for 48 hours resulting in complete hydrolysis (only partial hydrolysis was noted after 24 hours). The mixture was then acidified with concentrated HCl (to pH 2.5) diluted with brine (20 ml) and was extracted with ether (3×20 ml). The extracts were combined, washed with water (2×100 ml), dried (MgSO$_4$ anhydrous) and evaporated to afford the crude product as an oil (210 mg). This was subjected to a column chromatography on silica gel (Baker, 60–200 mesh, 10 g), eluting the column with hexane and Et$_2$O-hexane mixtures (15:85, 1:3) to isolate homogeneous (tlc) title acid as an oil (200 mg, 89%), $[\alpha]_D^{23}=(+) 1.16°$ (c, 2.2; CHCl$_3$), with consistent IR, MS, H$^1$- and C$^{13}$-NMR spectral data.

Anal Calcd for C$_{22}$H$_{38}$O$_4$ (MW 366.54): C, 72.08; H, 10.46. Found: C, 72.16; H, 10.37. This hydrolysis can be effected faster using a mixture of 1,4-dioxane and water as solvents at reflux temperature.

H$^1$-NMR Spectrum (FX-270, CDCl$_3$): δ 0.90 (t, 3H, J=~8.0, H$_{21}$); 1.23 (s, 6H, —, H$_{22}$+H$_{23}$); 2.03 (m, 4H, J=~8.0, H$_4$+H$_7$); 3.35 (m, 4H, J=~8.0, H$_{14}$+H$_{16}$); 4.2 (d, 1H, J=~4.0, H$_9$); 4.43 (d, 1H, J=~4.0, H$_{12}$); 5.35 (m, 1H, —, H$_5$+H$_6$);

M. [1R-[1α,2β(5Z),3β,4α]]-7-[3-[(Hexyloxy)-methyl]-7-oxabicyclo[2.2.1]hept-2-yl]-N-hydroxy-N,2,2-trimethyl-5-heptenamide A solution of Part L acid (300 mg; 0.82 mmole) in dry benzene (5.0 ml) was treated with oxalyl chloride (1 ml: 11.24 mmole or 13.7 eq.) and stirred at room temperature under nitrogen for 2 hours. The excess oxalyl chloride and solvent were blown off by a stream of nitrogen while heating the reaction flask in a warm water bath and the oil obtained dried in vacuo (oil pump) for 1 hour. The residual acid chloride was dissolved in dry tetrahydrofuran (1.5 ml) and added dropwise into a cold solution (0°, ice-water) of 98% methylhydroxylamine hydrochloride (139.8 mg; 1.64 mmole) and triethylamine (0.34 ml; 2.46 mmole) in tetrahydrofuran (2 ml) and water (2.0 ml). The mixture was stirred at 0° under nitrogen for 30 minutes and at room temperature for 5.5 hours, diluted with water (10 ml) and extracted twice with dichloromethane (50 ml). The organic extract was washed with 1N HCl (10 ml), 5% NaHCO$_3$ (5 ml) and water (10 ml), dried (anhydrous MgSO$_4$), filtered and evaporated to dryness giving an oil (290.5 mg) containing the desired product and traces of other components (TLC) including Part L acid. This material was treated with an excess of CH$_2$N$_2$ in Et$_2$O and stirred at room temperature for 45 minutes. The excess diazomethane was blown off with a stream of nitrogen and the clear solution evaporated to dryness. The residual oil was chromatographed (gravity) on a silica gel column (Baker 60-200 mesh; 40 ml), eluting the column with EtOAc:hexane (1:3, 400 ml). The resulting homogeneous oily product (167 mg) was combined with material (90 mg) obtained from a previous run. It was dissolved in ether (50 ml) and washed with 1N HCl, followed by water (10 ml) and brine (10 ml), dried (anhydrous MgSO$_4$) filtered and evaporated to dryness. The product, after drying in vacuo, gave the title hydroxamate as a homogeneous (TLC) oil with consistent elemental analysis, IR (1600, 1638 Cm$^{-1}$, strong, C=O, 3215 Cm$^{-1}$, strong, OH) MS, H$^1$- and C$^{13}$-NMR spectral data.

Anal Calcd for C$_{23}$H$_{41}$NO$_4$: C, 69.83; N, 10.45; N, 3.54. Found: C, 69.67; N, 10.51; N, 3.46.

H$^1$-NMR Spectrum (FX-270, CDCl$_3$): δ 0.89 (t, 3H, J=~8, H$_{21}$); 1.1-2.2 (m, 26H, —, —); 3.21-3.46 (m, 4H, H$_{14}$+H$_{16}$); 3.31 (s, 3H, H$_{24}$); 4.36 (d, 1H, J=~4, H$_9$); 4.48 (d, 1H, J=~4, H$_{12}$); 5.2-5.31 (m, 1H, —, H$_5$ or H$_6$); 5.45-5.57 (m, 1H, —, H$_5$ or H$_6$); 8.45 (s, broad, 1H, N-OH).

EXAMPLE 52

[1R-[1α,2β(Z),3β,4α]]-7-[3-[(Benzyloxy)methyl]-7-oxabicyclo[2.2.1]hept-2-yl]-N-hydroxy-N-butyl-5-heptenamide Following the procedure of Example 2 Parts A to H and Example 51 Part M except in Example 2 substituting benzyl mesylate for hexyl mesylate and in Example 51 Part M substituting the Example 2 acid for the Example 51 Part L acid and substituting butylhydroxyamine for methylhydroxyamine, the title compound is obtained.

EXAMPLE 53

[1R-[1α,2β(Z),3β,4α]]-7-[3-[(Cyclopropyloxy)methyl]-7-oxabicyclo[2.2.1]hept-2-yl]-N-hydroxy-5-heptenamide Following the procedure of Example 2 Parts A to H and Example 51 Part M except substituting cyclopropyl mesylate for hexyl mesylate and substituting the Example 2 acid for the Example 51 Part L acid, and substituting hydroxyamine for methylhydroxyamine, the title compound is obtained.

EXAMPLE 54

(1α,2β,3α,4α)-7-[3-[2-(Hexyloxy)ethyl]-7-oxabicyclo[2.2.1]hept-2-yl]-N-hydroxy-N-methyl-heptanamide Following the procedure of Example 30 and Example 51 Part M except substituting (1α,2β,-3β,4α)-7-[3-formyl-7-oxabicyclo[2.2.1]hept-2-yl]-heptanoic acid, methyl ester for [1α,2β(Z),3β,4α]-7-[3-formyl-7-oxabicyclo[2.2.1]hept-2-yl]-5-heptenoic acid, methyl ester, the title compound is obtained.

What is claimed is:

1. A compound having the structural formula

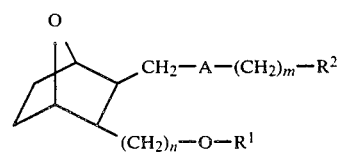

and including all stereoisomers thereof, wherein
A is —CH=CH— or —(CH$_2$)$_2$—;
m is 1 to 8; n is 1 to 4;
R$^1$ is lower alkyl, aryl, aralkyl, lower alkenyl containing 2 to 12 carbons, cycloalkyl or cycloalkylalkyl; and R$^2$ is

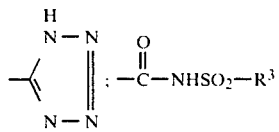

wherein R³ is aryl or arylalkyl; provided that where R² is

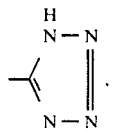

n is 1, wherein lower alkyl or alkyl alone or as part of another group contains 1 to 12 carbons and is unsubstituted or is substituted with halo, $CF_3$, alkoxy, alkylthio, alkylamino, alkylamino, haloaryl, cycloalkyl or alkylcycloalkyl;

aryl alone or as part of another group contains 6 to 10 carbons in the ring portion and is unsubstituted or is substituted with lower alkyl, halogen or lower alkoxy; and cycloalkyl alone or as part of another group contains 3 to 12 carbons and is unsubstituted or is substituted with 1 or 2 halogens, 1 or 2 lower alkyl groups and/or 1 or 2 lower alkoxy groups.

2. The compound as defined in claim 1 wherein A is —CH=CH—.

3. The compound as defined in claim 1 wherein R² is

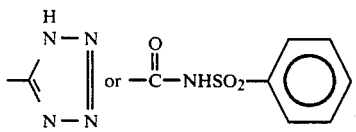

4. The compound as defined in claim 1 wherein n is 1.
5. The compound as defined in claim 1 wherein $(CH_2)_m$ is $(CH_2)_{2-5}$,

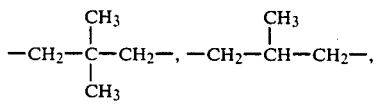

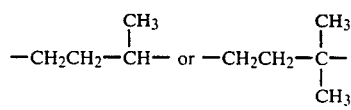

6. The compound as defined in claim 1 wherein $(CH_2)_m$ is $(CH_2)_3$.

7. The compound as defined in claim 1 wherein n is 1 and R¹ is methyl.

8. The compound as defined in claim 1 wherein A is —CH=CH—, m is 2 to 4, n is 1 or 2, R¹ is lower alkyl or cycloalkyl.

9. The compound as defined in claim 1 wherein A is —CH=CH—, m is 3, n is 1, R¹ is lower alkyl, and R² is

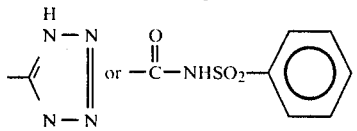

10. The compound as defined in claim 1 having the name [1β,2α(Z),3α,4β]-5-[6-[3-[(hexyloxy)methyl]-7-oxabicyclo[2.2.1]hept-2-yl]-4-hexenyl-1H-tetrazole, including all stereoisomers thereof.

11. The compound as defined in claim 1 having the name [1R-[1α,2β(Z),3β,4α]]-7-[3-[(hexyloxy)methyl]-7-oxabicyclo[2.2.1]hept-2-yl]-N-(phenylsulfonyl)-5-heptenamide, including all stereoisomers thereof.

12. A method of inhibiting platelet aggregation and bronchoconstriction, which comprises administering to the circulatory system of a mammalian host an effective amount of a compound as defined in claim 1 or a pharmaceutically acceptable salt thereof.

13. The method as defined in claim 12 wherein said compound is administered in an amount within the range of from about 1 to about 100 mg/kg.

14. A composition for inhibiting platelet aggregation and bronchoconstriction comprising an effective amount of a compound as defined in claim 1 or a pharmaceutically acceptable salt thereof, and a pharmaceutically acceptable carrier thereof.

15. A method of inhibiting platelet aggregation which comprises administering to a mammalian host an effective amount of a compound as defined in claim 1 or a pharmaceutically acceptable salt thereof.

16. A method of inhibiting bronchoconstriction associated with asthma, which comprises administering to a mammalian host an effective amount of a compound as defined in claim 1 or a pharmaceutically acceptable salt thereof.

17. A method for inhibiting platelet aggregation and bronchoconstriction by inhibiting production of thromboxane $A_2$ by blocking the action of thromboxane synthetase, which comprises administering to a mammalian host an effective amount of a compound as defined in claim 1 or a pharmaceutically acceptable salt thereof.

18. A method for treating inflammation in a mammalian species in need of such treatment, which comprises administering to a mammalian host an effective amount of a compound as defined in claim 1 or a pharmaceutically acceptable salt thereof.

19. A method of relieving pain in a mammalian specie, which comprises administering to said mammalian specie a composition containing an analgesically effective amount of a compound as defined in claim 1 or a pharmaceutically acceptable salt thereof.

* * * * *